US009968305B1

(12) United States Patent
Brown et al.

(10) Patent No.: US 9,968,305 B1
(45) Date of Patent: May 15, 2018

(54) SYSTEM AND METHOD OF GENERATING MUSIC FROM ELECTRICAL ACTIVITY DATA

(71) Applicants: James S Brown, Odessa (CA); Brian Lorne Fisher, Camden East (CA)

(72) Inventors: James S Brown, Odessa (CA); Brian Lorne Fisher, Camden East (CA)

(*) Notice: Subject to any disclaimer, the term of this patent is extended or adjusted under 35 U.S.C. 154(b) by 139 days.

(21) Appl. No.: 14/873,408

(22) Filed: Oct. 2, 2015

Related U.S. Application Data

(60) Provisional application No. 62/058,711, filed on Oct. 2, 2014.

(51) Int. Cl.
| | |
|---|---|
| *G10H 1/36* | (2006.01) |
| *A61B 5/00* | (2006.01) |
| *A61B 5/053* | (2006.01) |
| *G01N 33/00* | (2006.01) |
| *G01D 5/12* | (2006.01) |
| *G01N 33/483* | (2006.01) |
| *G10H 5/00* | (2006.01) |

(52) U.S. Cl.
CPC .......... *A61B 5/7415* (2013.01); *A61B 5/0531* (2013.01); *G01D 5/12* (2013.01); *G01N 33/0098* (2013.01); *G01N 33/483* (2013.01); *G10H 5/005* (2013.01); *A61B 2503/12* (2013.01); *A61B 2503/40* (2013.01); *G10H 2210/111* (2013.01); *G10H 2210/141* (2013.01); *G10H 2210/251* (2013.01); *G10H 2220/371* (2013.01)

(58) Field of Classification Search
CPC . A61B 5/7415; A61B 5/0531; A61B 2503/12; A61B 2503/40; G01D 5/12; G01N 33/483; G10H 5/005; G10H 2210/111; G10H 2210/141; G10H 2210/251; G10H 2220/371
USPC .......................................................... 84/634
See application file for complete search history.

(56) References Cited

U.S. PATENT DOCUMENTS

| | | | | |
|---|---|---|---|---|
| 5,253,168 A | * | 10/1993 | Berg ..................... | A61B 5/4857 128/905 |
| 6,487,817 B2 | * | 12/2002 | Airaudi ................... | A61B 5/05 47/1.3 |
| 6,743,164 B2 | * | 6/2004 | Airaudi ................... | A01G 7/00 47/1.3 |
| 8,242,344 B2 | * | 8/2012 | Moffatt ................ | G10H 1/0008 84/609 |

(Continued)

*Primary Examiner* — Jeffrey Donels
(74) *Attorney, Agent, or Firm* — Rick B. Yeager

(57) ABSTRACT

The Plant Choir™ system comprises a software program and hardware that measures electrical activity of a person, plant, or animal and translates those readings into music on a computing device. The system gathers electrical activity data using electrodermal activity (EDA) measurement devices. The EDA readings of the individual subjects are translated via the software into musical melodies in real time. The individual subject melodies are combined to create interesting harmonies similar to a choir. The music is rendered using a MIDI (Musical Instrument Data Interface) programming interface of the computer operating system. The software allows the user to select program options, set music and program parameters. Variations in the EDA signal are interpreted as music. Each subject connected to the system is assigned a musical voice and the voices are combined to create multi part harmonies similar to a choir.

8 Claims, 5 Drawing Sheets

Plant Choir(tm) Block Diagram

(56) References Cited

U.S. PATENT DOCUMENTS

| | | | |
|---|---|---|---|
| 2002/0026746 A1* | 3/2002 | Airaudi | A61B 5/05 47/17 |
| 2003/0106260 A1* | 6/2003 | Airaudi | A01G 7/00 47/58.1 LS |
| 2006/0111621 A1* | 5/2006 | Coppi | A61B 5/222 600/300 |
| 2016/0198984 A1* | 7/2016 | Daniele | A61B 5/145 600/309 |

* cited by examiner

FIG. 1 - Plant Chum(tm) Block Diagram

SYSTEM AND METHOD OF GENERATING MUSIC FROM ELECTRICAL ACTIVITY DATA

RELATED APPLICATIONS

This US non-provisional patent application is related to U.S. Provisional Application No. 62/058,711 filed Oct. 2, 2014 and claims the priority of that filing date.

BACKGROUND

Field of the Invention

The present invention relates to the acquisition of electrical activity readings from multiple subjects such as persons, plants or animals for the purpose of translating those readings into music in real time. The music that is created by each of the subjects is combined to form interesting harmonies similar to a choir.

Prior Art

Electrodermal Activity (EDA) refers to the electrical properties of the skin which are directly affected by changes in sweat gland activity. Psychologists have long been using EDA data to determine the emotional responses of subjects to external stimuli such as investigative questions.

Plants respond similarly to external stimuli such as physical touch and changes in heat, light, and moisture. This results in a change in the electrical activity of the plant as measured by the EDA device.

SUMMARY

In one embodiment, the Plant Choir™ system comprises a software program and hardware that measures electrical activity of a person, plant, or animal and translates those readings into music on a computing device. The system gathers electrical activity data using proprietary Limestone Technologies DataPac_EDA™ electrodermal activity (EDA) measurement devices. The EDA readings of the individual subjects are translated via the software into musical melodies in real time. The individual subject melodies are combined to create interesting harmonies similar to a choir. The music is rendered using a MIDI (Musical Instrument Data Interface) programming interface of the computer operating system. The software allows the user to select program options, set music and program parameters.

Variations in the EDA signal are interpreted as music. Each subject connected to the system is assigned a musical voice and the voices are combined to create multi part harmonies similar to a choir.

DESCRIPTION OF EMBODIMENT—PLANT CHOIR™ SYSTEM

Figure 1:
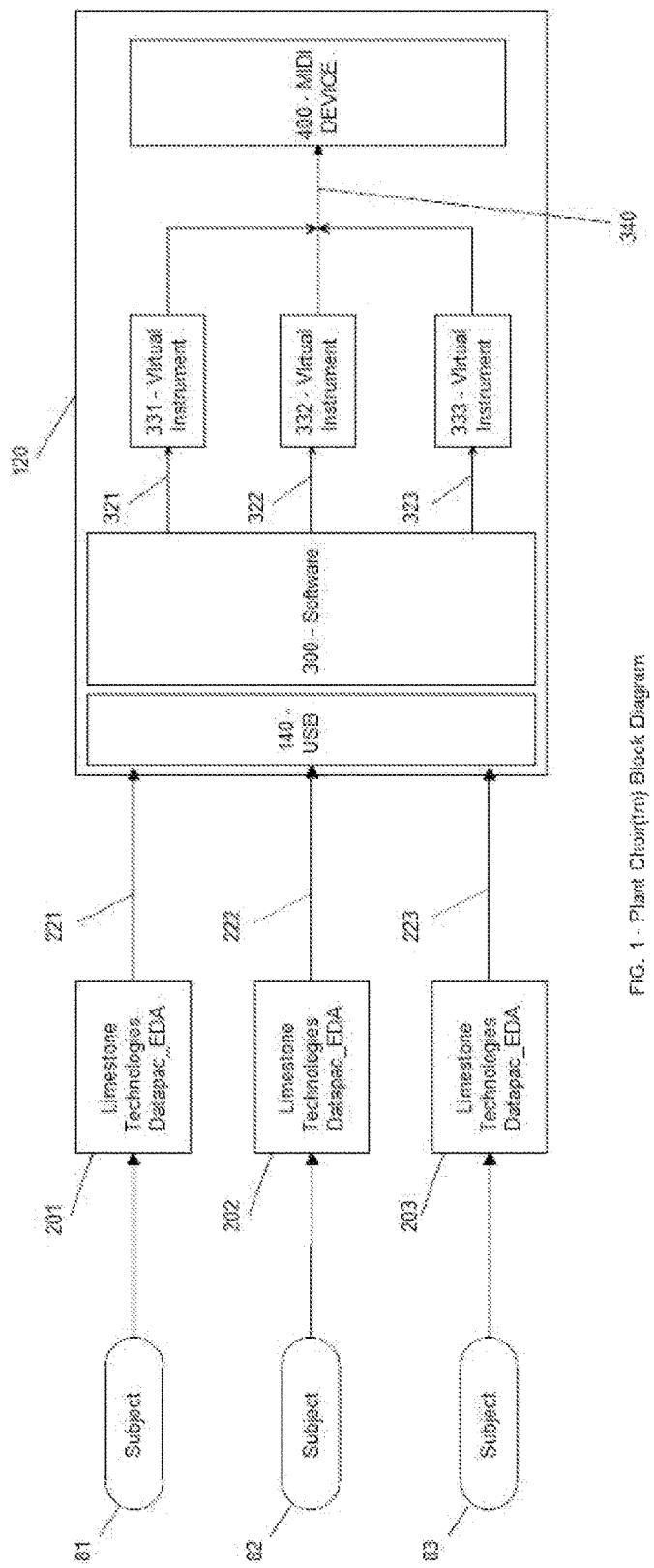
FIG. 1 is a block diagram of an embodiment of the Plant Choir hardware and software system.

FIG. 1 is a system diagram of an example embodiment of a Plant Choir™ system 100 for generating music from a plurality of subjects 81, 82, and 83. In some examples, the subjects may be plants, animals, people, or combinations thereof. In the example of FIG. 1, there are 3 subjects. In general, the system comprises any number of two or more subjects.

In FIG. 1, EDA devices 201, 202, and 203 are connected to subjects 81, 82, and 83 respectively. The EDA devices provide raw data steams 221, 222, and 223, respectively, to a computer 120. In this example, the data is provided through a USB (Universal Serial Bus) connection 140.

The computer runs software 300 to convert the raw data streams to sequences of musical notes 321, 322, and 323. In this specification, the term "musical notes" refers to individual notes or combinations of notes such as chords. The musical notes are generated according to various virtual music instruments 321, 322, and 323 which are assigned to each subject.

The computer combines the sequences of musical notes to a combined output stream 340. The output stream 340 is converted to audible music by a MIDI device 400.

Software Options

Figure 2:
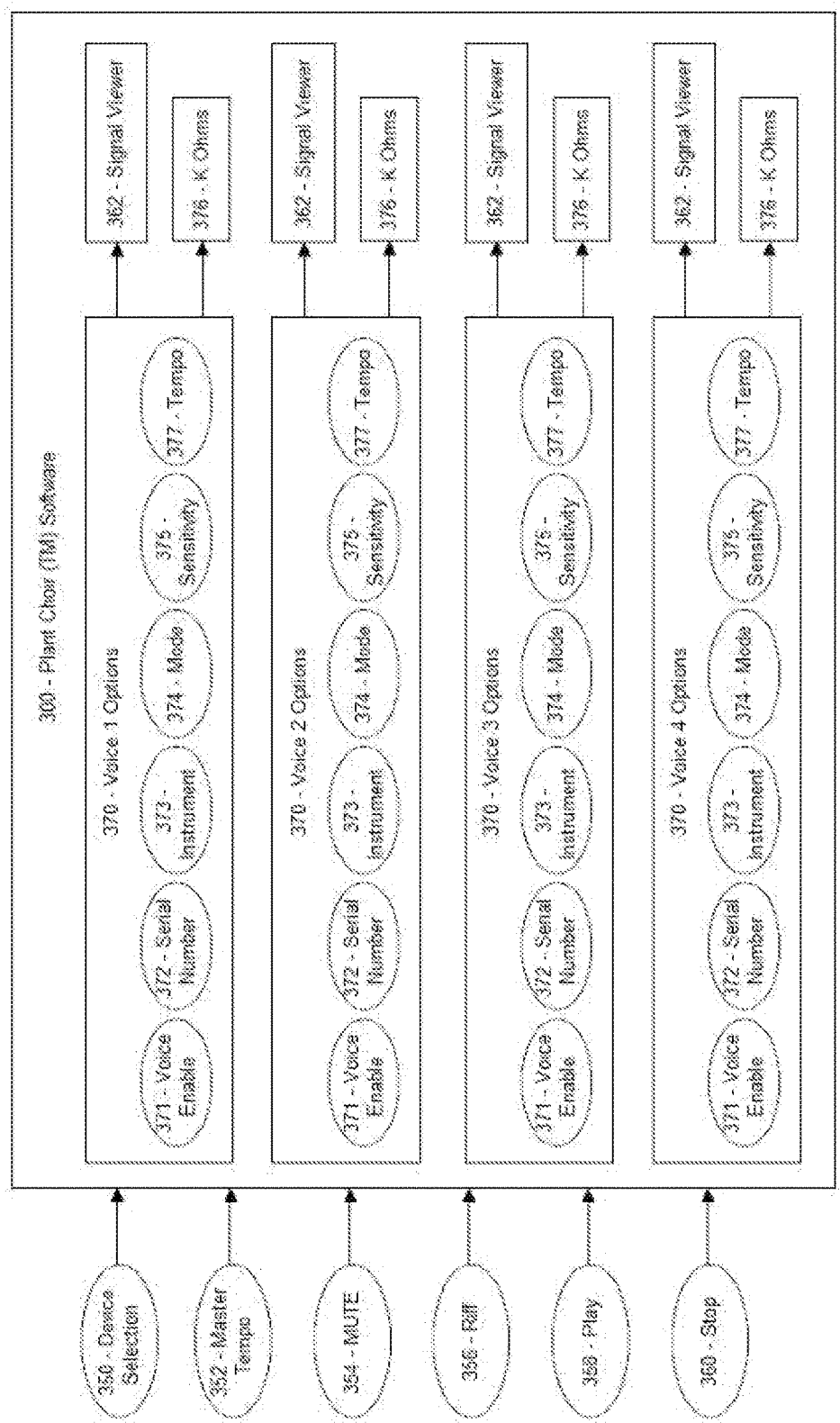
FIG. 2 is a block diagram of the Plant Choir software in the system of FIG. 1.

FIG. 2 is a block diagram of the software 300 in the Plant Choir system 100 of FIG. 1. In this embodiment, the Plant Choir software allows the user to set the following parameters:

Device Selection 350—The user may select the MIDI output device used to render the music. The default device is the Microsoft GS Wavetable Synth which ultimately drives speakers attached to the personal computer. The operating system will recognize other MIDI output devices if they are installed in or connected to the computer system.

Master Tempo 352—The user may determine the tempo of the melodies that are produced. A checkbox is provided to disable this feature in order to allow each individual 'voice' to be assigned its own independent tempo.

Mute 354—The user may mute or silence the music playback.

Riff 356—This allows the computer to select the notes to be played in a more random fashion in order to make the melodies more interesting.

Play 358—This button or control starts the playback conversion of input into music.

Stop 360—This button or control stops the playback conversion of input into music.

Signal Viewer 362—This control is used to display the electrodermal response signal variations being produced by each individual subject.

Voice Options 370—In one embodiment, Plant Choir is able to accommodate four Limestone Technologies DataPac_EDA units. Each unit is mapped to a 'voice' in the choir for which there are independent settings and parameters:

Voice enable checkbox 371—This control enables or disables the voice from producing sound.

Serial Number 372—This control maps the voice to a specific Limestone Technologies DataPac_EDA device.

Instrument 373—This control determines the MIDI instrument that will be used to render music for the voice.

Mode 374—This control selects the scale or set of notes that will be used by a particular voice. In this embodiment, the following sets of notes are available: Major, Pentatonic, Chromatic, Blues, and Percussion.

Sensitivity 375—This control is a threshold value that determines when the voice will sound in response to the EDA input signal.

kohms 376—This indicator is a readout of the current resistance value of the subject between the EDA device electrodes. It is a measure of the quality of the electrical connection to the subject.

Tempo 377—If the Master Tempo enable checkbox is unchecked, then each voice is allowed to play at its own tempo. Each voice may then be assigned a different tempo in order to produce interesting rhythm combinations.

Setup and Operation

Figure 3:
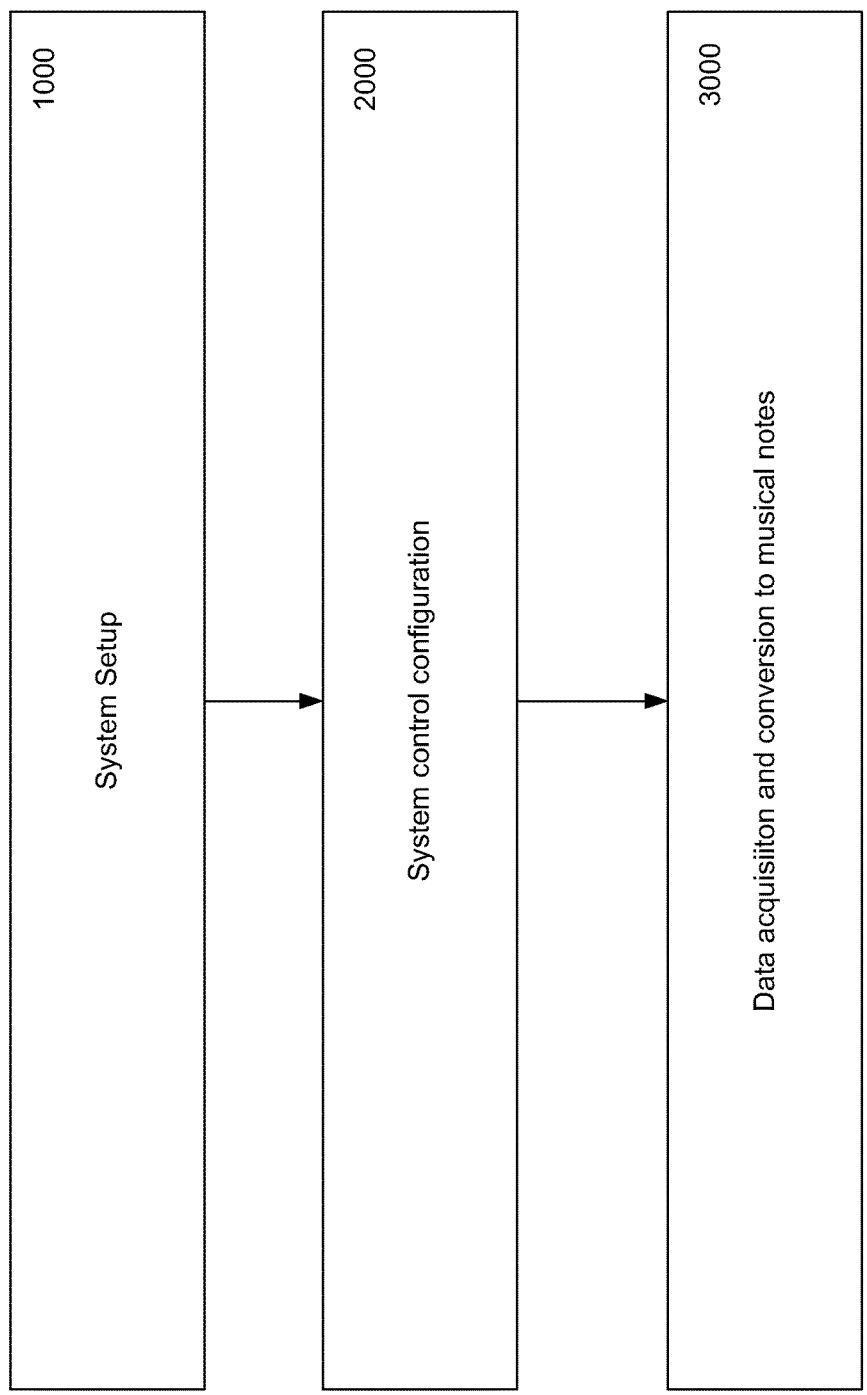
FIG. 3 is a flow diagram of an example setup and control for the system of FIG. 1.

FIG. 3 is a flow diagram of an example setup and control for the system of FIG. 1.

At Step 1000, the system is setup. EDA devices 201, 202, and 203 are connected to individual subjects 81, 82, and 83. Each EDA device 201, 202, and 203 is connected to the computer 120.

At Step 2000, the system controls are configured by the user. The user selects, or the system defaults to, an output device selection 350, master tempo 352, riff 356. During operation, the user may select play 358, stop 360, mute 354, and signal viewer 362. The user selects, or the system defaults to, voice options 370 for each subject.

At Step 3000, the system acquires EDA data and converts the data to musical notes.

Figure 4:
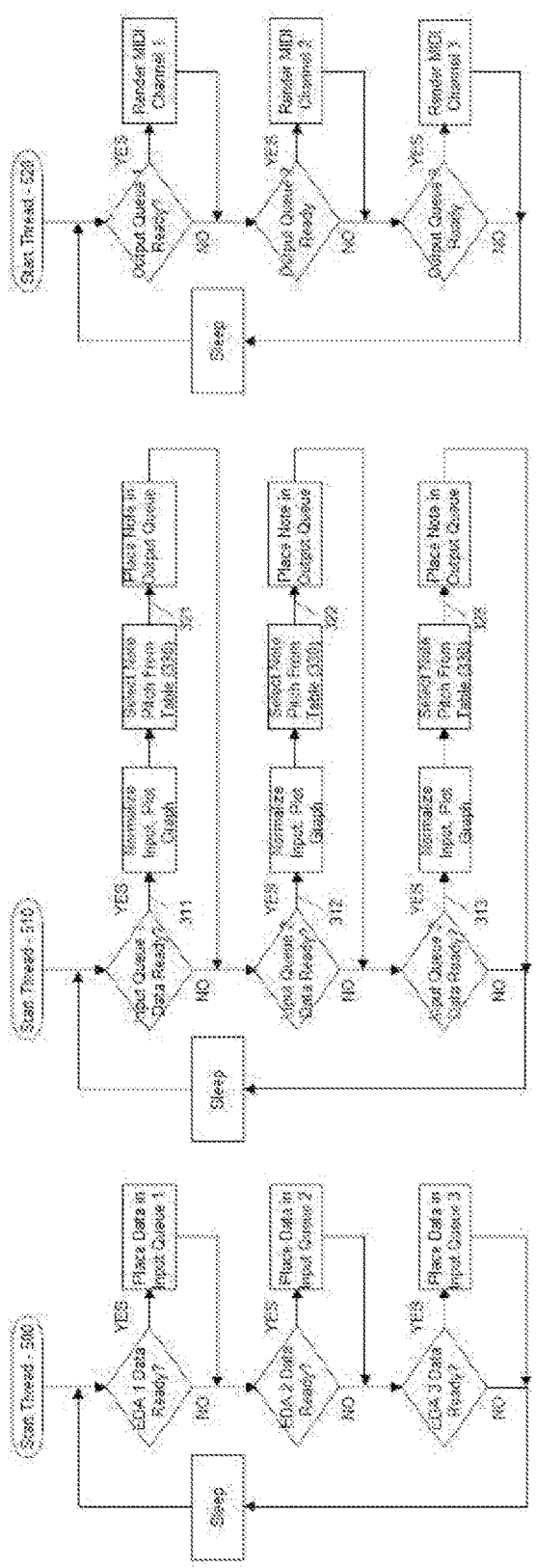
FIG. 4 is a software and logic diagram of FIG. 1.

FIG. 4 is a software logic diagram for the system of FIG. 1. A background thread 500 running within the Plant Choir software gathers data from the DataPac_USB devices as the data becomes available and places the data in its respective Input Queue.

A second thread running 510 within the Plant Choir software is responsible for removing samples from the Input Queue and translating those values into musical notes through the use of a lookup table 530.

The software normalizes each input signal 311, 312, 313 to automatically compensate for changes in the input signal amplitude. The normalized input values are used to select notes 321, 322, and 323 from a lookup table 330. The lookup table assigned to each 'voice" is configurable within the software and may contain note pitch values for a variety of musical modes such as major, minor, chromatic, pentatonic, blues, percussion, and custom subsets, for example.

A note structure is created which contains information such as pitch, tempo, volume, instrument, and effects. Once the parameters of the note have been determined, the note structure is placed in an Output Queue to await rendering by the MIDI output module as sound.

At step 4000, the individual musical notes are combined and played as an audible concert.

A third thread 520 running within Plant Choir is responsible for removing notes from the Output Queue and rendering them via the MIDI interface. In the standard program configuration the music is rendered through the computer operating system's MIDI interface and the sound is directed to the computer speakers.

If an external MIDI interface is attached or installed in the computer system the software can be configured to render its output on that device instead of the default Windows device, allowing for the attachment of external synthesizers.

In this embodiment, a system of software and proprietary hardware is used to acquire EDA readings from multiple subjects in order to produce music in multi-part harmony in a fashion similar to a choir.

Each DataPac_EDA device samples the subject's surface conductance at fixed intervals and transmits the readings to a personal computer via a USB (Universal Serial Bus) connection. One DataPac_EDA device is used per subject and multiple DataPac_EDA devices may be used to connect multiple subjects to the personal computer system.

Figure 5:
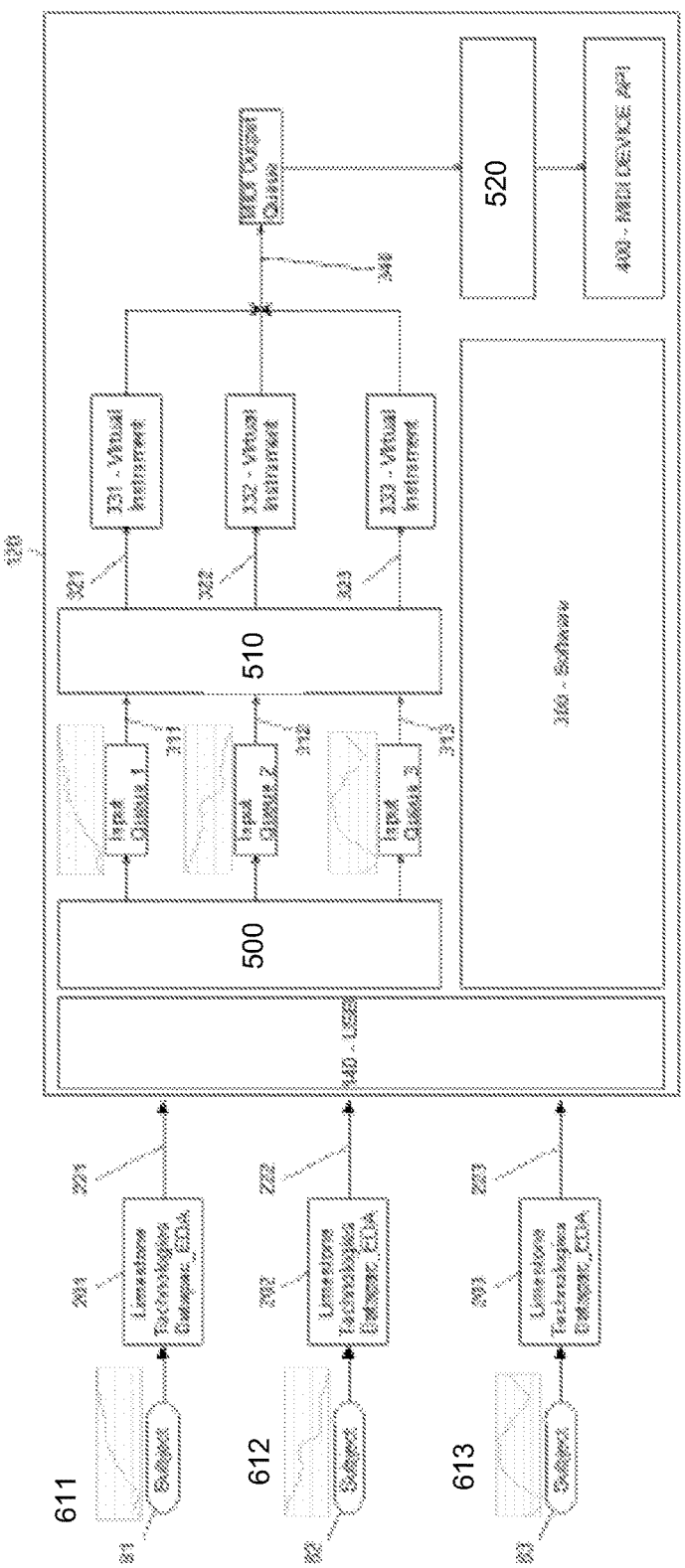
FIG. 5 is an example detailed block diagram of an embodiment of the Plant Choir hardware and software system.

FIG. 5 is an example detailed block diagram of an embodiment of the Plant Choir hardware and software system. In this example, subject 81 is a plant with an example input EDA waveform 611; subject 82 is a dog with an example input EDA waveform 612; and subject 83 is a human with an example input EDA waveform 613. Background thread 500 gathers the EDA data from the EDA devices for each subject and places the data in the respective input queues 311, 312, and 313. Second thread 510 removes the EDA data from the Input Queues and translates those values into musical notes through the use of a lookup table 530 (not shown). Third thread 520 removes the combined notes from MIDI Output Queue 340 and feeds the MIDI device API 400. A virtual structure containing information about the note's value and duration is created and placed in an output queue. Thread 320 de-queues the virtual note items and plays the notes through a MIDI application programmers interface, in a manner similar to striking a note on a keyboard or synthesizer.

It is to be understood that the specific embodiments and examples described above are by way of illustration, and not limitation. Various modifications may be made by one of ordinary skill, and the scope of the invention is defined in the appended claims.

What is claimed is:

1. A method for generating music from the electrical activity data of multiple subjects, the method comprising connecting a plurality of electrodermal activity devices to a plurality of subjects, such that each electrodermal activity device is connected to a subject;

connecting each electrodermal activity device to a computing device;

providing electrodermal activity signal conversion software on the computing device;

configuring the electrodermal activity signal conversion software;

acquiring electrodermal activity data signals from each subject;

converting the EDA data signal from each subject to a musical note; and simultaneously playing the musical notes from each subject on an output device.

2. The method of claim 1 wherein configuring the electrodermal activity signal conversion software further comprises accepting user input for desired voice options.

3. The method of claim 2 wherein accepting user input for desired voice options further comprises mapping a voice to a specific electrodermal activity device.

4. The method of claim 2 wherein accepting user input for desired voice options further comprises accepting one or more of a voice enablement option, a sensitivity threshold,
an individual voice or selecting of a master tempo, and a note set for a voice.

5. The method of claim 1 wherein configuring the electrodermal activity signal conversion software further comprises
accepting user input for a desired tempo.

6. The method of claim 1 wherein acquiring electrodermal activity data signals from each subject further comprises
storing electrodermal activity data signals from a subject in an input queue.

7. The method of claim 6 wherein converting the electrodermal activity data signal from each subject to a musical note further comprises
removing electrodermal activity data signals from the input queue;
normalizing the electrodermal activity data signals; and
translating the electrodermal activity data signals into musical notes through the use of a lookup table.

8. The method of claim 1 further comprising displaying electrodermal response signal variations for each subject.

\* \* \* \* \*